(12) United States Patent
Kimura et al.

(10) Patent No.: US 12,310,874 B2
(45) Date of Patent: May 27, 2025

(54) WEARABLE ASSIST DEVICE

(71) Applicant: Mazda Motor Corporation, Hiroshima (JP)

(72) Inventors: Yoshiaki Kimura, Hiroshima (JP); Hisashi Watanuki, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 303 days.

(21) Appl. No.: 18/126,480

(22) Filed: Mar. 27, 2023

(65) Prior Publication Data

US 2023/0320887 A1 Oct. 12, 2023

(30) Foreign Application Priority Data

Apr. 12, 2022 (JP) ................. 2022-065803

(51) Int. Cl.
*A61F 5/02* (2006.01)

(52) U.S. Cl.
CPC .............. *A61F 5/028* (2013.01); *A61F 5/026* (2013.01)

(58) Field of Classification Search
CPC .. A61F 5/028; A61F 5/026; A61F 5/02; A61F 5/013; A61F 2005/0155; A61F 2005/0146; A61F 2005/0167; A61F 2005/0137; B25J 9/0006; B25J 9/00; B25J 9/109; B25J 9/10; B25J 9/101; B25J 9/0009; B25J 19/0008; F16M 13/04
USPC ............................................. 602/19
See application file for complete search history.

(56) References Cited

U.S. PATENT DOCUMENTS

| | | |
|---|---|---|
| 2015/0316204 A1 | 11/2015 | Doyle |
| 2016/0058597 A1* | 3/2016 | Williams ............... A61F 5/028 602/19 |
| 2016/0363264 A1 | 12/2016 | Doyle |
| 2019/0249825 A1 | 8/2019 | Doyle |

FOREIGN PATENT DOCUMENTS

JP 2017-512666 A 5/2017

\* cited by examiner

*Primary Examiner* — Alireza Nia
*Assistant Examiner* — Daniel A Miller
(74) *Attorney, Agent, or Firm* — XSENSUS LLP

(57) ABSTRACT

To provide an assist device capable of suitably providing an assist force to a worker even when an upper extremity is positioned relatively low, an assist device capable of generating an assist force for a worker includes a supporting portion capable of supporting an armpit of the worker, wherein the supporting portion is arranged to be independent of a motion of an upper extremity of the worker, and wherein the supporting portion is a reaction force receiving portion against a load force of a grasped object by the worker.

18 Claims, 16 Drawing Sheets

WEARABLE ASSIST DEVICE

CROSS-REFERENCE TO RELATED APPLICATION

The present application claims priority to Japanese Patent Application No. 2022-065803, filed on Apr. 12, 2022, the entire contents of which are incorporated herein by reference.

BACKGROUND

Field

The present disclosure relates to an assist device. In particular, the present disclosure relates to a wearable assist device that can be worn on a worker.

Description of the Related Art

In recent years, a technique for allowing a worker to wear an assist device and perform work is actively introduced to reduce a workload and improve the work environment, for example. The assist device is capable of providing an assist force to a worker holding a workpiece, while supporting an upper extremity of the worker by a supporting portion that is a component of the assist device.

CITATION LIST

Patent Literature

[Patent Literature 1] National Publication of International Patent Application No. 2017-512666

SUMMARY

Problems to be Solved

Here, the inventors of the present application have newly found that a conventional assist device has the following points to be improved. Specifically, in an example in which the upper extremity of the worker is supported by the supporting portion of the conventional assist device, it may not be easy to provide an assist force to the worker when the angle formed by the upper extremity of the worker and the trunk of the worker is less than a predetermined angle (for example, 45 degrees), that is, when the upper extremity of the worker is positioned relatively low.

Therefore, an object of the present disclosure is to provide an assist device capable of suitably providing an assist force to the worker even when the upper extremity is positioned relatively low.

Solutions to the Problems

In order to achieve the object described above, the present disclosure provides an assist device capable of generating an assist force for a worker, and including a supporting portion capable of supporting an armpit of the worker.

Advantages

According to an embodiment of the present disclosure, it is possible to suitably provide the assist force to the worker even when the upper extremity is positioned relatively low.

DETAILED DESCRIPTION

Figure 1:
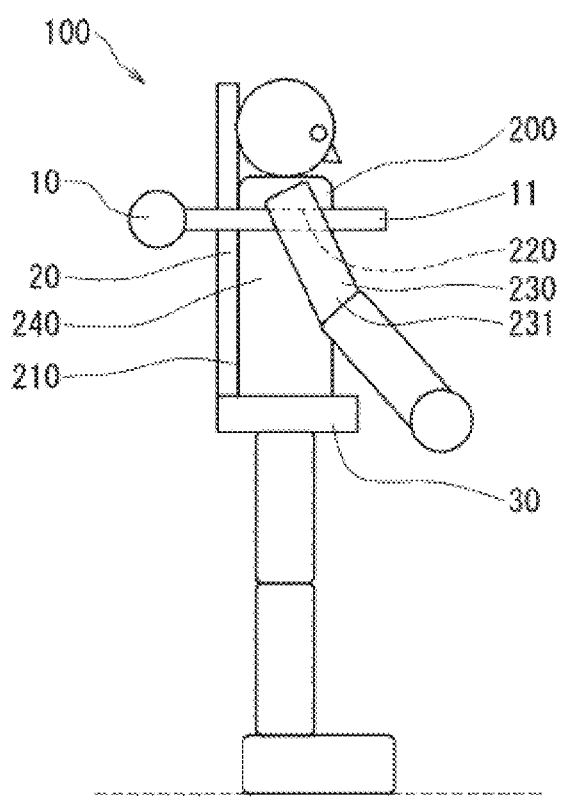
FIG. 1 is a side view schematically showing an assist device according to one or more aspects of the present disclosure.

Hereinafter, an assist device according to the present disclosure will be described in detail with reference to the drawings. Various elements in the drawings are schematically and exemplary shown only for facilitating understanding of the present disclosure, and the appearance, dimensional ratios, etc. may be different in the actual elements.

[Configuration of Assist Device]

Hereinafter, a configuration of the assist device according to one or more aspects of the present disclosure will be described.

As described above, the inventors of the present application have newly found that, when the upper extremity of the worker is supported by the supporting portion of the conventional assist device, it may not be easy to provide an assist force to the worker when the angle formed by the upper extremity of the worker and the trunk of the worker is less than a predetermined angle (for example, 45 degrees), that is, when the upper extremity of the worker is positioned relatively low.

Then, instead of solving the problem by an extension of the conventional technique of supporting the upper extremity of the worker by the supporting portion, the inventors of the present application have eagerly considered a solution using a technique different from the conventional technique. As a result, the inventors of the present application have found that an armpit of the worker is the part that is difficult to follow a motion of the upper extremity. Accordingly, one or more aspects of the present disclosure include supporting the armpit of the worker rather than the upper extremity of the worker (see FIG. 1). Note that the "upper extremity" mentioned in the present description means the part including the upper arm, forearm, hand, etc. of the worker.

Figure 2:
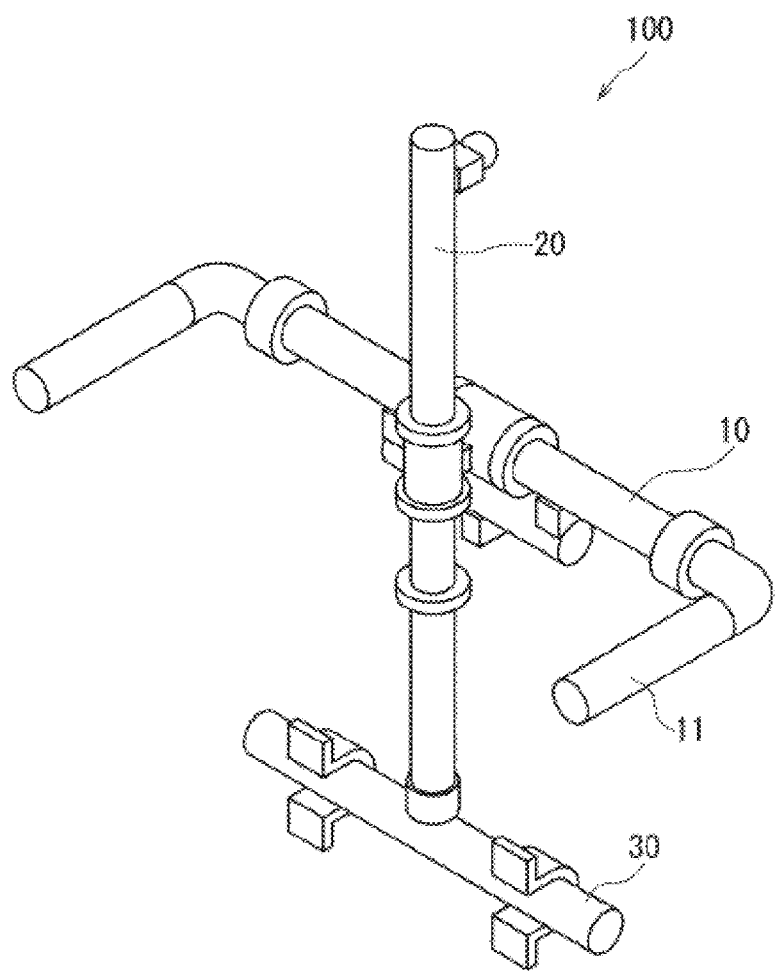
FIG. 2 is a perspective view schematically showing the assist device according to one or more aspects of the present disclosure.
Figure 3:
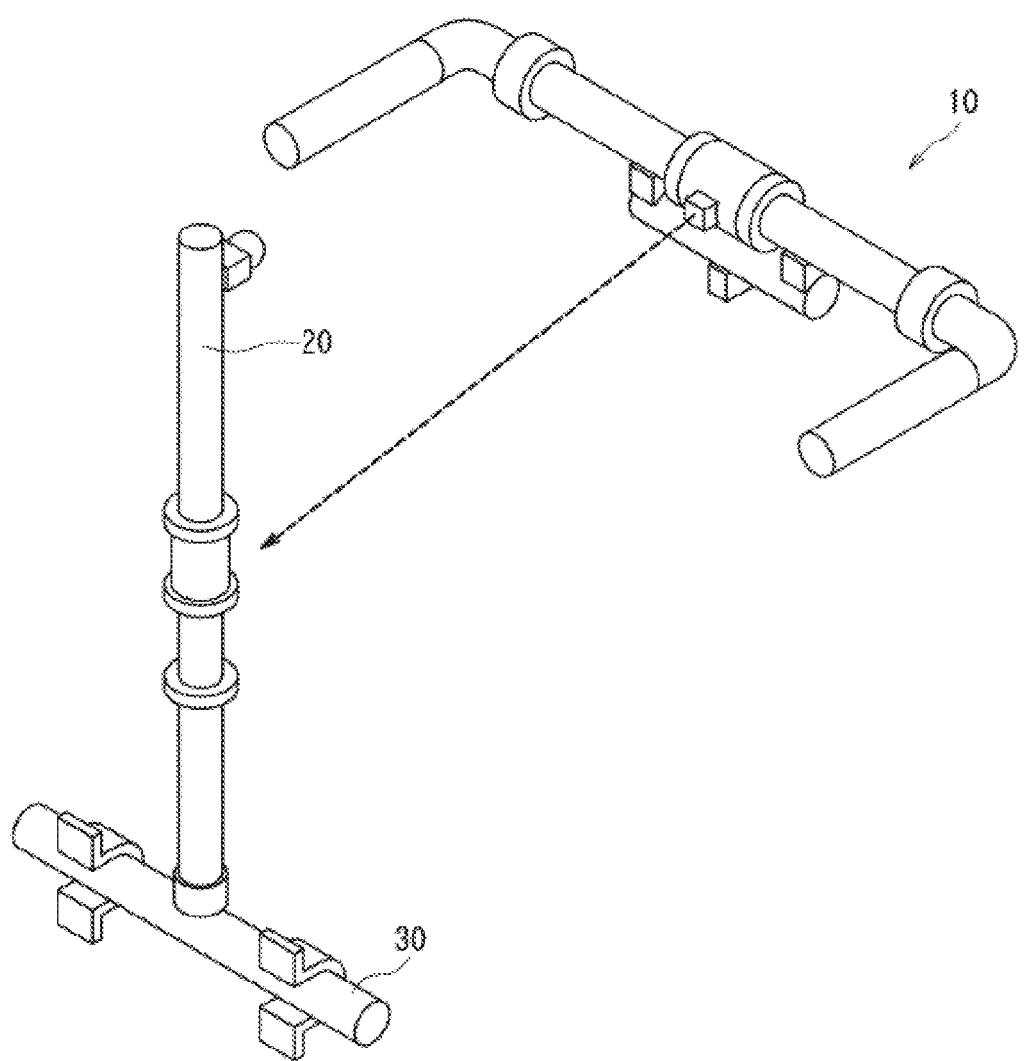
FIG. 3 is an exploded perspective view schematically showing the assist device according to one or more aspects of the present disclosure.
Figure 4:
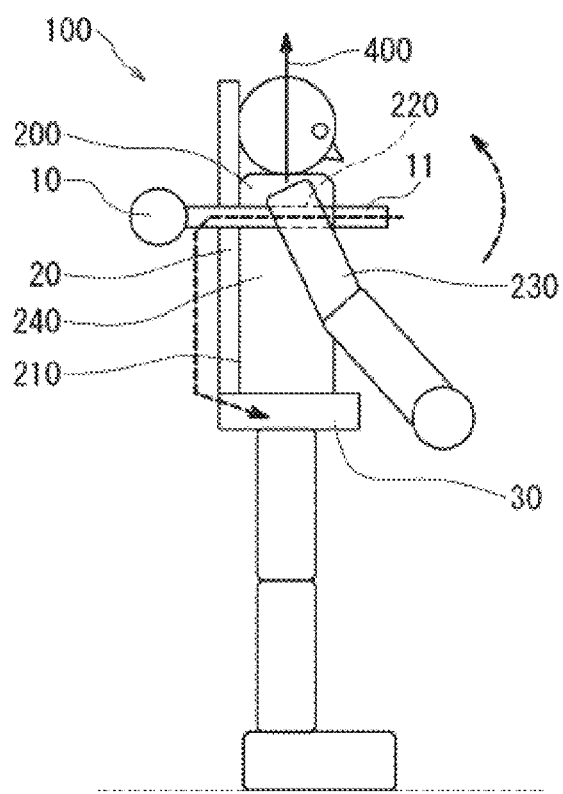
FIG. 4 is a side view schematically showing a transmission path of a reaction force generated in the assist device according to one or more aspects of the present disclosure.
Figure 5:
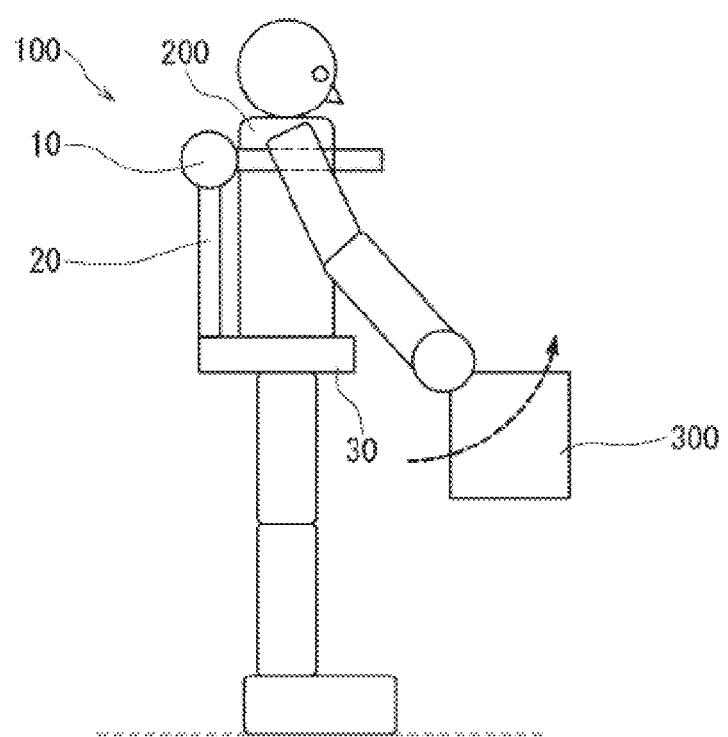
FIG. 5 is an exemplary side view schematic in which a workpiece is grasped using the assist device according to one or more aspects of the present disclosure.
Figure 6:
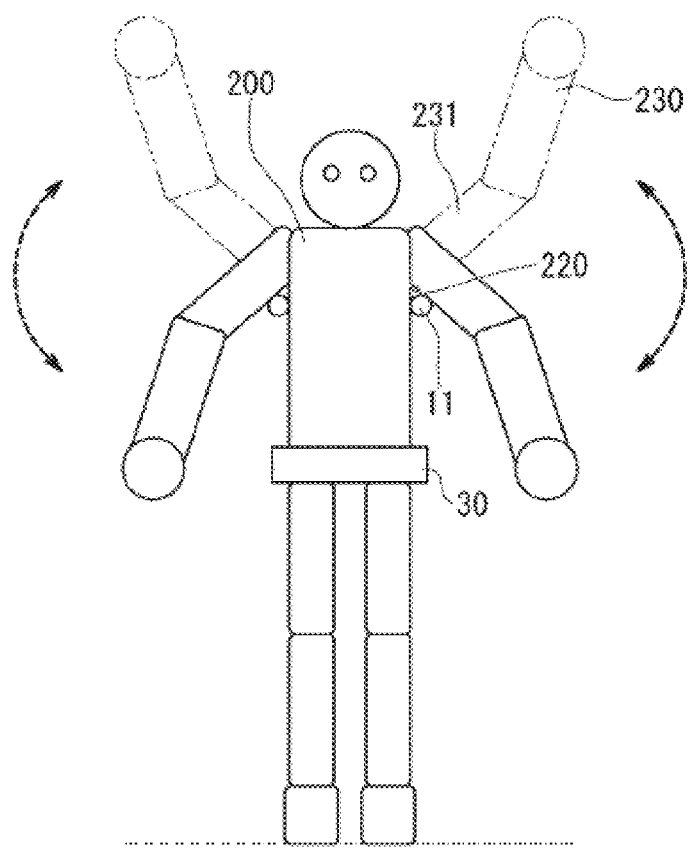
FIG. 6 is a front view schematically showing the assist device according to one or more aspects of the present disclosure.

FIG. 1 is a side view schematically showing the assist device according to one or more aspects of the present disclosure. FIG. 2 is a perspective view schematically showing the assist device according to one or more aspects of the present disclosure. FIG. 3 is an exploded perspective view schematically showing the assist device according to one or more aspects of the present disclosure. FIG. 4 is a side view schematically showing a transmission path of a reaction force generated in the assist device according to one or more aspects of the present disclosure. FIG. 5 is a side view schematically showing an example in which a workpiece is grasped using the assist device according to one or more aspects of the present disclosure. FIG. 6 is a front view schematically showing the assist device according to one or more aspects of the present disclosure.

An assist device 100 according to one or more aspects of the present disclosure can be used as a so-called "wearable" device that is worn on a worker 200 (see FIG. 1, etc.). The assist device 100 according to one or more aspects of the present disclosure has an arm portion 10 including a supporting portion 11; a supporting pole portion 20 connected to the arm portion 10; and a wearable portion 30 connected the supporting pole portion 20 and wearable on the worker 200 (see FIG. 1 to FIG. 3). In one example, the arm portion 10 can be arranged to surround the back of the worker 200 and a side of a trunk 240.

The supporting portion 11 can be, for example, a long cylindrical member. Moreover, the supporting pole portion 20 extends along a back 210 of the worker 200, specifically along a longitudinal direction of the back 210. In this case, the arm portion 10 and the supporting pole portion 20 can be arranged to intersect each other, for example, in the form of a cross. Although there are no particular limitations, the arm portion 10, the supporting pole portion 20, and the wearable portion 30 can be formed from, for example, a carbon material, and a connecting portion of the respective components can be formed from a material such as aluminum.

An embodiment of the present disclosure is characterized in that the supporting portion 11 is capable of supporting an armpit 220 of the worker 200. In the present description, the "armpit 220 of the worker 200" is the part located between the trunk 240 and an upper extremity 230 of the worker 200, and is the part with an outer surface extending in a direction intersecting the direction of gravity (equivalent to the vertical direction). In the present description, "the supporting portion 11 capable of supporting the armpit 220 of the worker 200" means a state in which the armpit is supported by the supporting portion 11 and/or a state in which the armpit is held by the supporting portion 11, and means a state in which the supporting portion 11 and the armpit 220 contact each other directly, or indirectly via a later-described shock absorbing member.

According to this characteristic, as described above, since the armpit 220 of the worker 200 is the part difficult to follow a motion of the upper extremity 230, it is also difficult for the supporting portion 11, which is supporting the armpit 220, to follow the motion of the upper extremity 230. Therefore, the supporting portion 11 can be arranged to be independent of the motion of the upper extremity 230 of the worker 200 (see FIG. 6). In other words, it is possible to avoid a movement of the supporting portion 11 following the motion of the upper extremity 230.

Moreover, the supporting portion 11 which is supporting the armpit 220 can take a form extending in the direction intersecting the direction of gravity in conforming to the form of the outer surface of the armpit 220. For example, if the supporting portion 11 is long, the longitudinal part thereof can extend in the direction intersecting the direction of gravity. Preferably, from the viewpoint of conforming to the form of the outer surface of a main part of the armpit 220, the supporting portion 11 can be arranged directly below the armpit 220.

From the above, since the movement of the supporting portion 11 following the motion of the upper extremity 230 can be avoided, it is possible to reduce a change of the supporting portion 11 in the extending direction intersecting the direction of gravity, in comparison with the conventional mode (the mode in which the upper extremity of the worker is supported by the supporting portion).

Consequently, in heavy muscular work performed in a state in which the supporting portion 11 and the armpit 220 contact each other (including heavy muscular work performed with the upper extremity 230 positioned relatively low) and/or also in work performed in a forward leaning posture, a reaction force in an opposite direction to the direction of gravity can be suitably generated at the supporting portion 11 by the contact of the armpit 220 and the supporting portion 11 positioned under the armpit 220 (see FIG. 4). Note that in heavy muscular work with the upper extremity 230 positioned relatively low, the supporting portion 11 can function as a receiving portion for a reaction force 400 against a load force of a grasped object (such as a workpiece 300 and a tool) by the worker 200 (see FIG. 5). For example, when the supporting portion 11 extends in a direction perpendicular to the direction of gravity, the supporting portion 11 can function as the receiving portion for the reaction force 400 generated toward the opposite direction to the acting direction of the load force of the grasped object along the direction of gravity.

In the present description, "work in which the upper extremity 230 of the worker 200 is likely to be positioned relatively low" means work which is performed in a state in which the supporting portion 11 and the armpit 220 can be in contact with each other, for example, work in which an angle θ formed by the trunk 240 and an upper arm 231 of the worker 200 is 0 degree<θ<120 degrees. Moreover, in the present description, "heavy muscular work performed with the upper extremity of the worker positioned relatively low" includes transport work of a heavy object of not less than 5 kg and not more than 25 kg.

Thus, with the assist device 100 according to one or more aspects of the present disclosure, even when the upper extremity 230 is positioned relatively low, it is possible to suitably provide an assist force to the worker 200 when the armpit 220 of the worker 200 is supported by the supporting portion 11. Note that, from the viewpoint of suitably providing the assist force described above during work using both upper extremities 230, it is preferred that the supporting portion 11 be capable of supporting both of the two armpits 220 of the worker 200.

Further, as described above, since the movement of the supporting portion 11 following the motion of the upper extremity 230 can be avoided, it is possible to suitably avoid contact of the supporting portion 11 and a surrounding object, such as a workpiece positioned around the supporting portion 11, in comparison with the conventional mode (the mode in which the upper extremity of the worker is supported by the supporting portion).

Furthermore, as described above, since the supporting pole portion 20 is connected to the arm portion 10 including the supporting portion 11, and the wearable portion 30 is connected to the supporting pole portion 20, these supporting pole portion 20 and wearable portion 30 can function as a reaction force transmitting portion against a load force of the grasped object (such as a workpiece and a tool) by the worker 200.

Consequently, the reaction force against the load force of the grasped object which is generated at the supporting portion 11 can be dispersed from the supporting portion 11 side to the wearable portion 30 side via the supporting pole portion 20. As a result, it is possible to reduce the load on the trunk 240 of the worker 200, that is, on muscles of the core of the body, and to reduce the load on the lumbar spine of the worker 200. Therefore, it is possible to improve the work efficiency of the worker 200.

Hereinafter, one or more aspects of the present disclosure will be further described.

First, the supporting portion 11 can be arranged to protrude along a side of the trunk 240 of the worker 200 to the front of the trunk 240.

According to this arrangement, since the supporting portion 11 is along the side of the trunk 240 of the worker 200, it is possible to suitably avoid contact of the supporting portion 11 and a surrounding object, such as a workpiece positioned around the supporting portion 11. Moreover, it is possible to suitably secure the contact state between the armpit 220 and the supporting portion 11.

Figure 7:
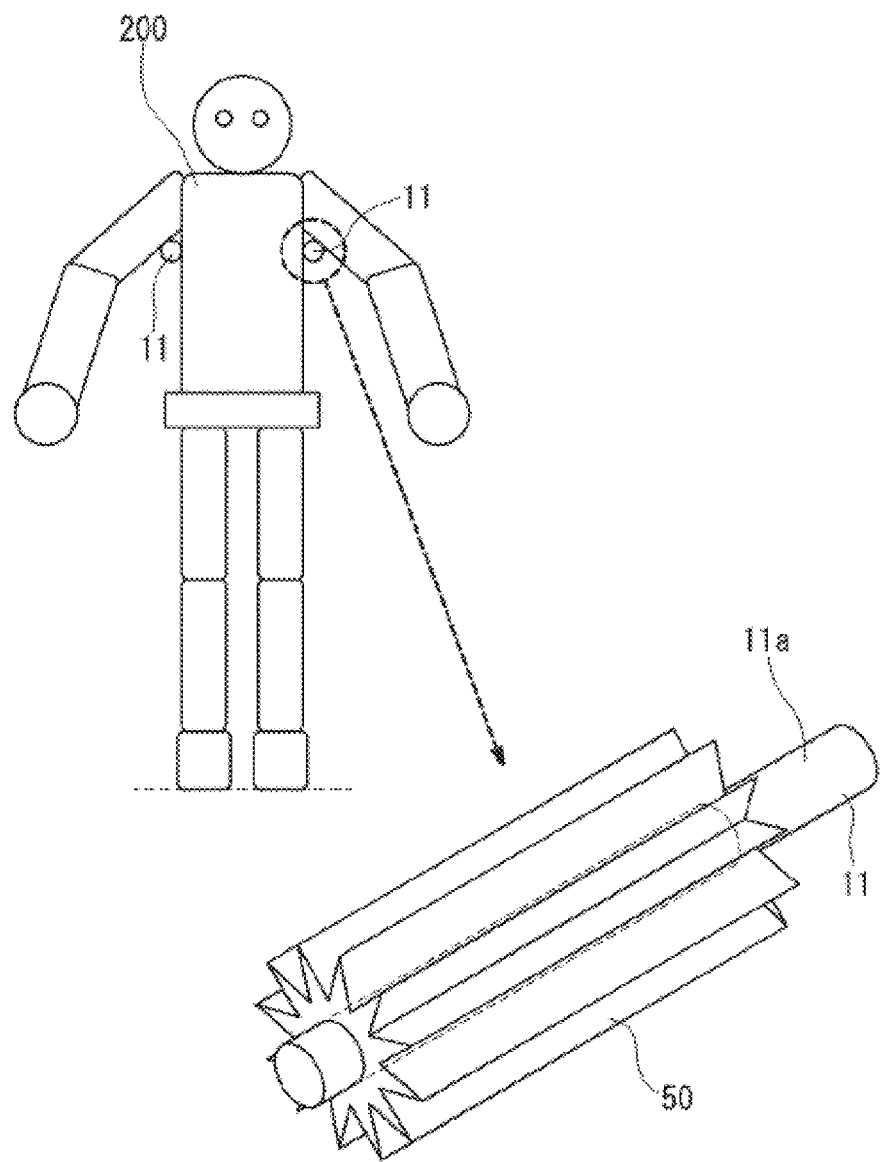
FIG. 7 is an enlarged perspective view schematically showing a supporting portion that is a component of the assist device according to one or more aspects of the present disclosure, and is directly surrounded by a shock absorbing member.
Figure 8:
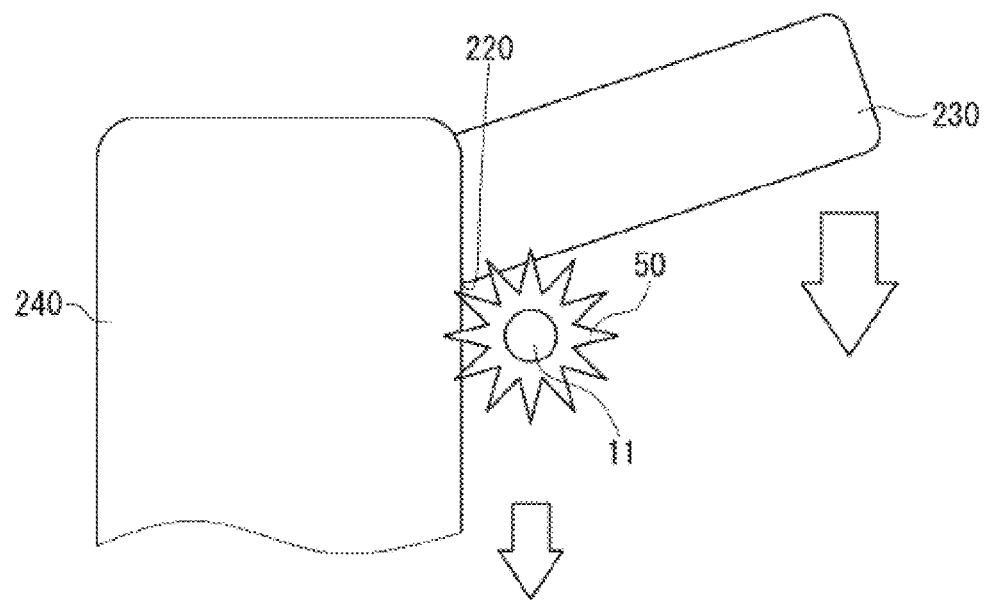
FIG. 8 is a partially enlarged front view schematically showing the supporting portion with the shock absorbing member of FIG. 7 in a state in which an upper extremity of a worker is positioned relatively high.
Figure 9:
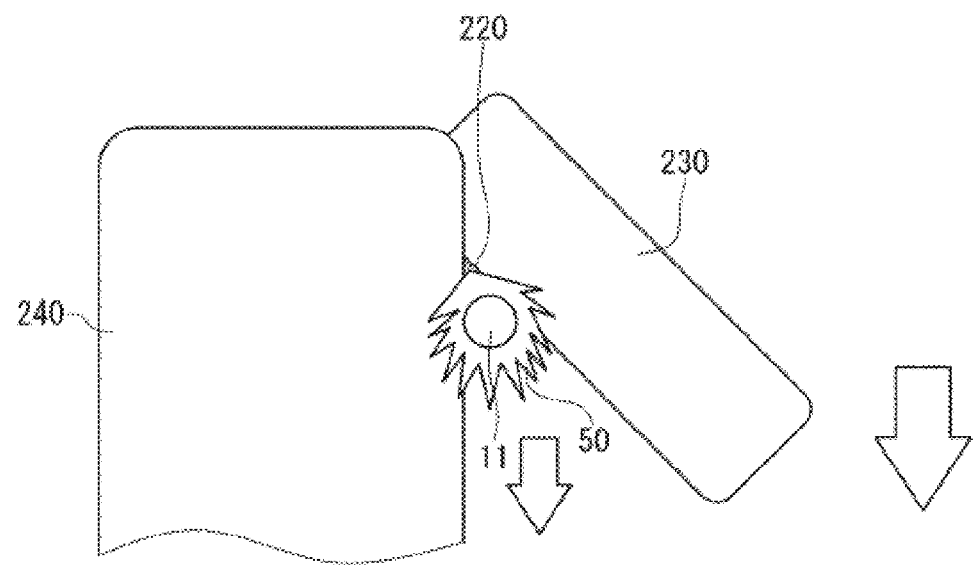
FIG. 9 is a partially enlarged front view schematically showing the supporting portion with the shock absorbing member of FIG. 7 in a state in which the upper extremity of the worker is positioned relatively low.

Additionally, a shock absorbing member 50 that surrounds an outer main surface 11a of the supporting portion 11 can be included (see FIG. 7 to FIG. 9).

FIG. 7 is an enlarged perspective view schematically showing the supporting portion that is a component of the assist device according to one or more aspects of the present disclosure, and is directly surrounded by the shock absorbing member. FIG. 8 is a partially enlarged front view schematically showing the supporting portion with the shock absorbing member of FIG. 7 in a state in which the upper extremity of the worker is positioned relatively high. FIG. 9 is a partially enlarged front view schematically showing the supporting portion with the shock absorbing member of FIG. 7 in a state in which the upper extremity of the worker is positioned relatively low.

For example, the outer main surface 11a of the supporting portion 11 is surrounded by the shock absorbing member 50. Specifically, the outer main surface 11a of the supporting portion 11 is directly surrounded by the shock absorbing member 50. In one example, the shock absorbing member 50 is an elastic cushion member.

According to the above characteristic, in comparison with a case in which the shock absorbing member 50 is not present, when the upper extremity 230 of the worker 200 is positioned either relatively high or relatively low during the use of the assist device, it is possible to reduce friction that is caused between the armpit 220 and the supporting portion 11 when supporting the armpit 220 by the supporting portion 11. Consequently, it is possible to suitably prevent occurrence of pain in the worker 200 during work, and to smoothly perform work using the assist force of the assist device.

Figure 10:
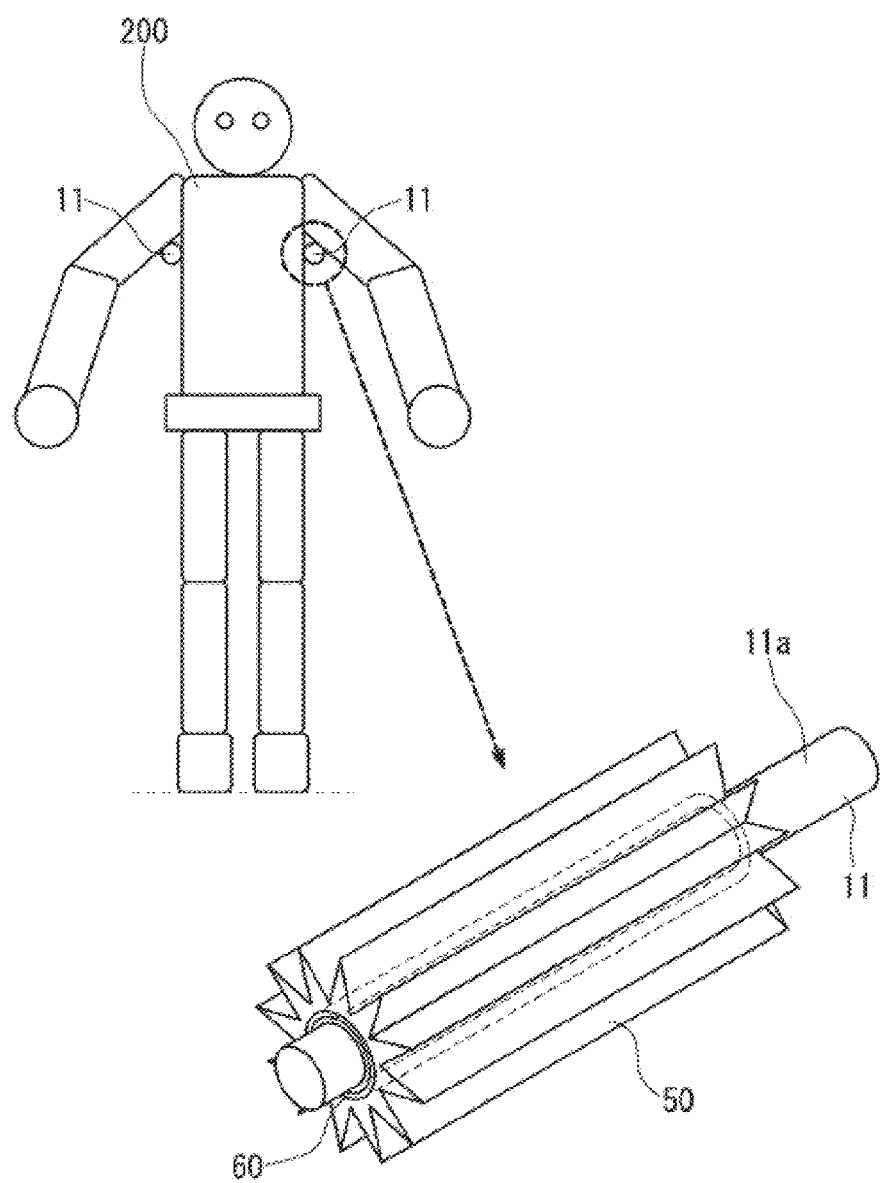
FIG. 10 is an enlarged perspective view schematically showing the supporting portion that is a component of the assist device according to one or more aspects of the present disclosure, and is indirectly surrounded by the shock absorbing member.
Figure 11:
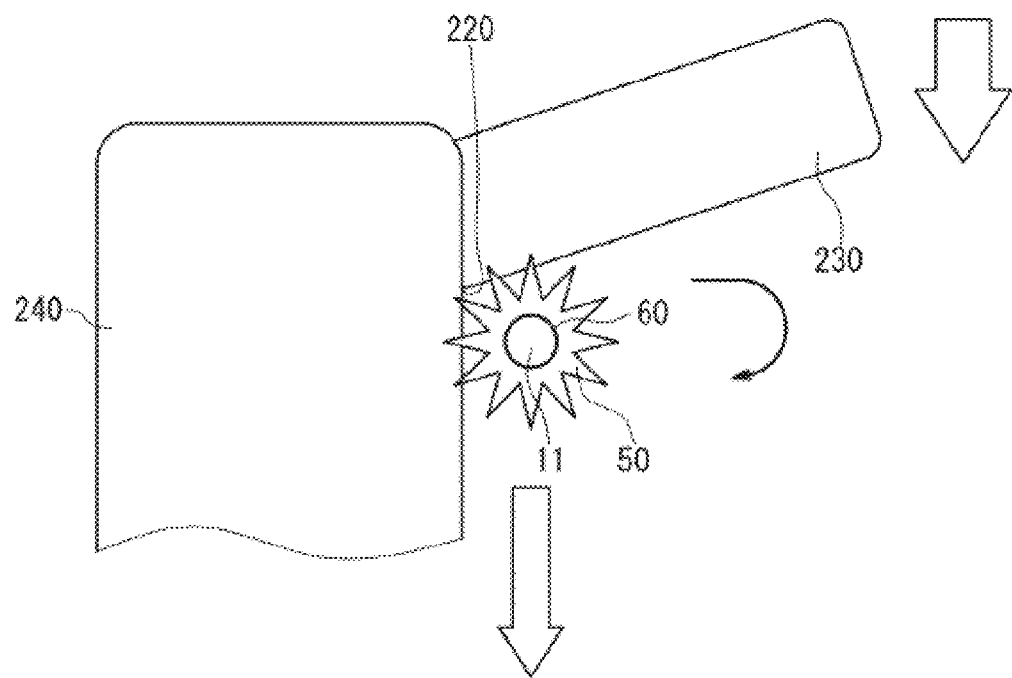
FIG. 11 is a partially enlarged front view schematically showing the supporting portion with the shock absorbing member of FIG. 10 in a state in which the upper extremity of the worker is positioned relatively high.
Figure 12:
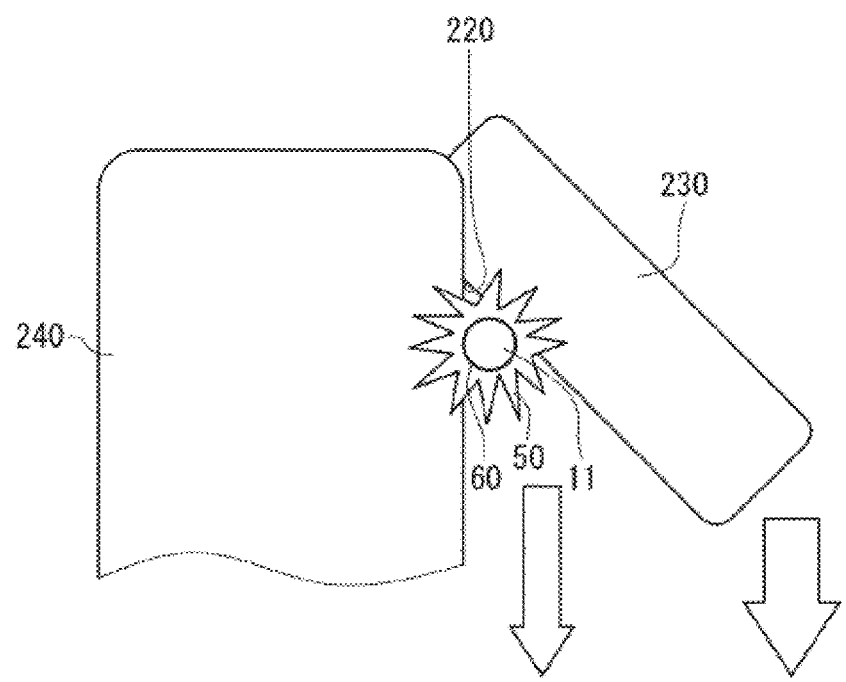
FIG. 12 is a partially enlarged front view schematically showing the supporting portion with the shock absorbing member of FIG. 10 in a state in which the upper extremity of the worker is positioned relatively low.

Additionally, an axially rotatable cylindrical portion 60 surrounding the outer main surface 11a of the supporting portion 11 can be included, and the shock absorbing member 50 surrounds the cylindrical portion 60 (see FIG. 10 to FIG. 12).

FIG. 10 is an enlarged perspective view schematically showing the supporting portion that is a component of the assist device according to one or more aspects of the present disclosure, and is indirectly surrounded by the shock absorbing member. FIG. 11 is a partially enlarged front view schematically showing the supporting portion with the shock absorbing member of FIG. 10 in a state in which the upper extremity of the worker is positioned relatively high. FIG. 12 is a partially enlarged front view schematically showing the supporting portion with the shock absorbing member of FIG. 10 in a state in which the upper extremity of the worker is positioned relatively low.

For example, the cylindrical portion 60 positioned over the outer main surface 11a of the supporting portion 11 is surrounded by the shock absorbing member 50. In short, the outer main surface 11a of the supporting portion 11 is indirectly surrounded by the shock absorbing member 50.

According to the above characteristic, in comparison with the case in which the outer main surface 11a of the supporting portion 11 is directly surrounded by the shock absorbing member 50, when the upper extremity 230 of the worker 200 is positioned either relatively high or relatively low during the use of the assist device, the cylindrical portion 60 interposed between the supporting portion 11 and the shock absorbing member 50 can axially rotate when supporting the armpit 220 by the supporting portion 11. Consequently, it is possible to further reduce friction that is caused between the armpit 220 and the supporting portion 11. As a result, it is possible to suitably prevent occurrence of pain in the worker 200 during work, and to perform work more smoothly using the assist force of the assist device.

Figure 13:
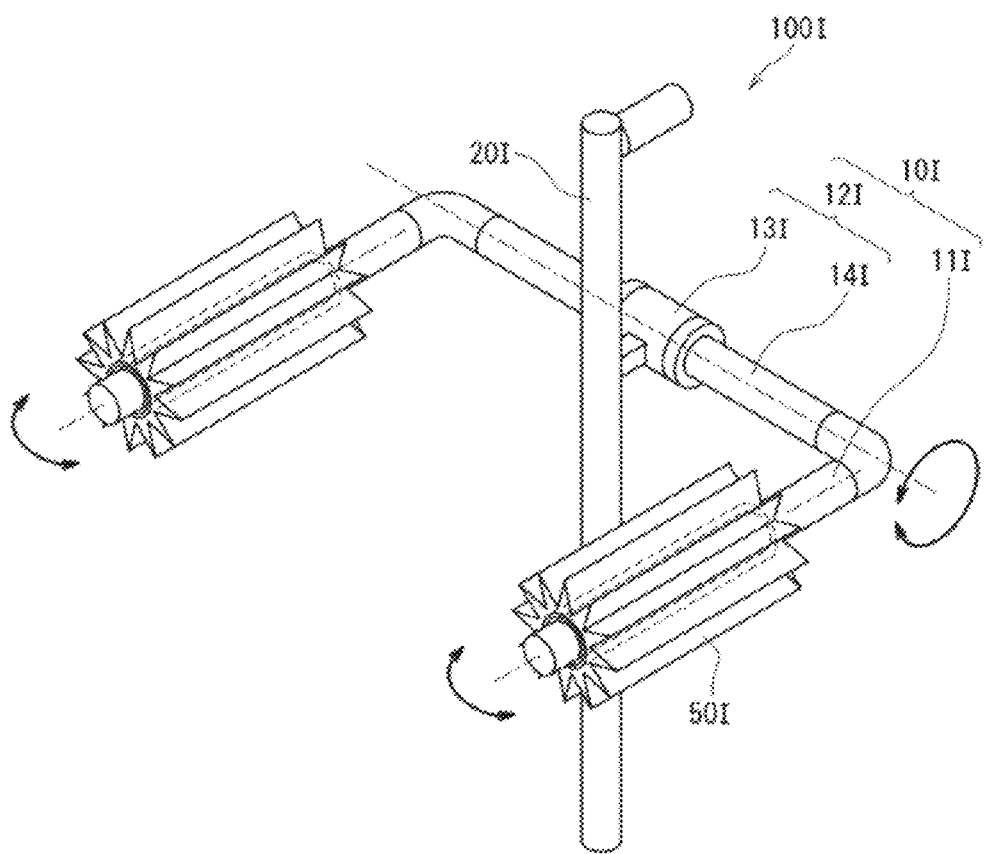
FIG. 13 is a perspective view schematically showing an example in which each arm portion that is a component of the assist device according to one or more aspects of the present disclosure is moved in an up-down direction.
Figure 14:
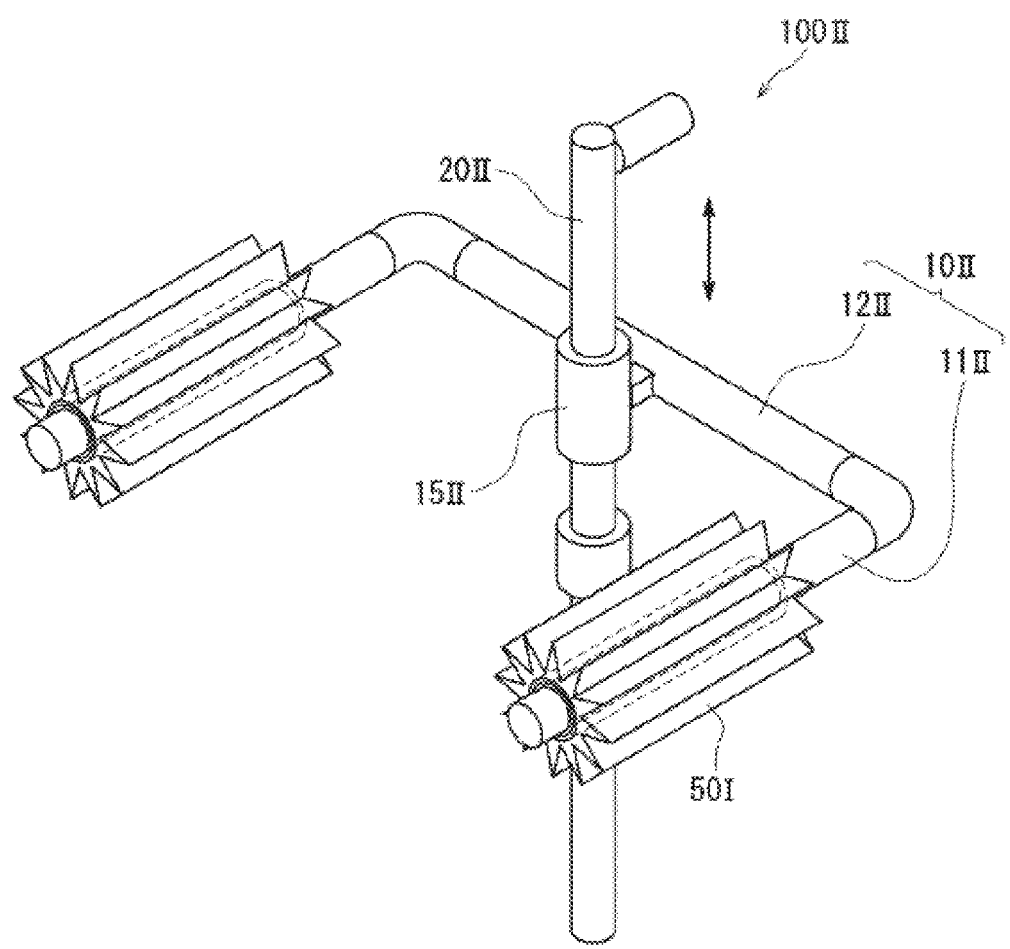
FIG. 14 is a perspective view schematically showing another example in which each arm portion that is a component of the assist device according to one or more aspects of the present disclosure is moved in the up-down direction.
Figure 15:
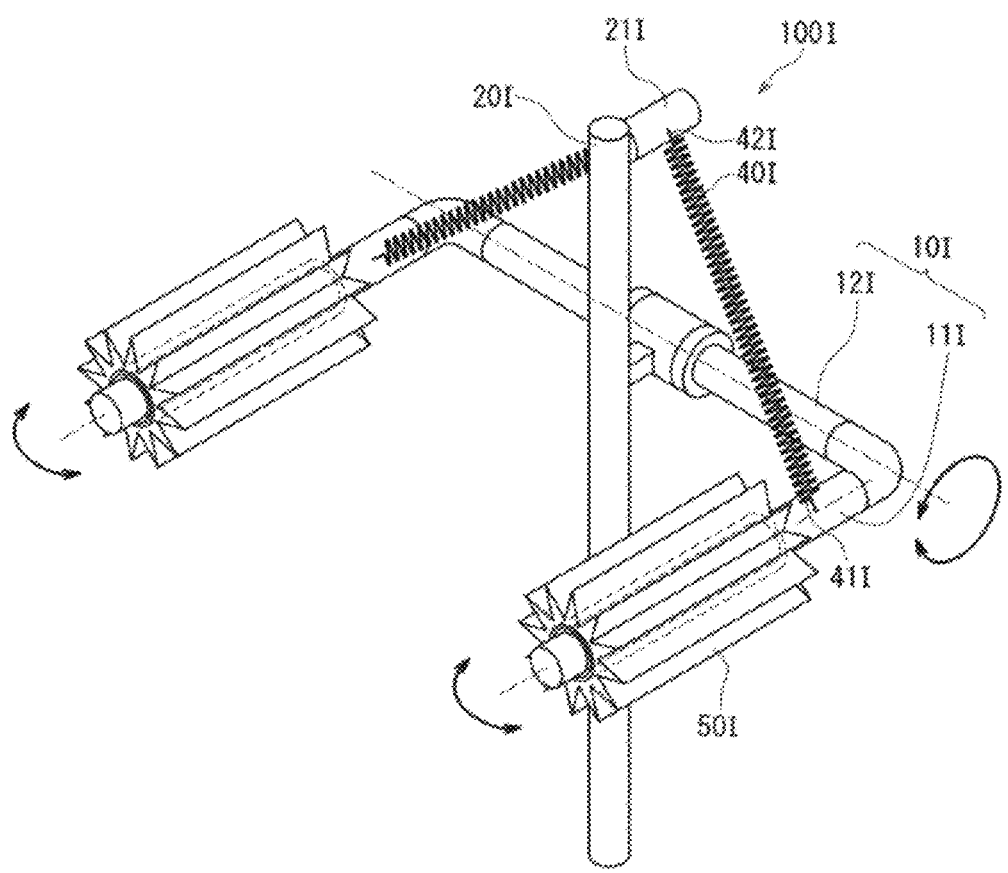
FIG. 15 is a perspective view schematically showing an example in which each arm portion that is a component of the assist device according to one or more aspects of the present disclosure is connected to an elastic portion.

For example, the arm portion 10 can be capable of moving up and down along the longitudinally extending direction of the supporting pole portion 20, and contacting or connecting to an elastic portion 40 that provides an elastic force in the opposite direction to the direction of gravity (see FIG. 13 to FIG. 15).

Figure 16:
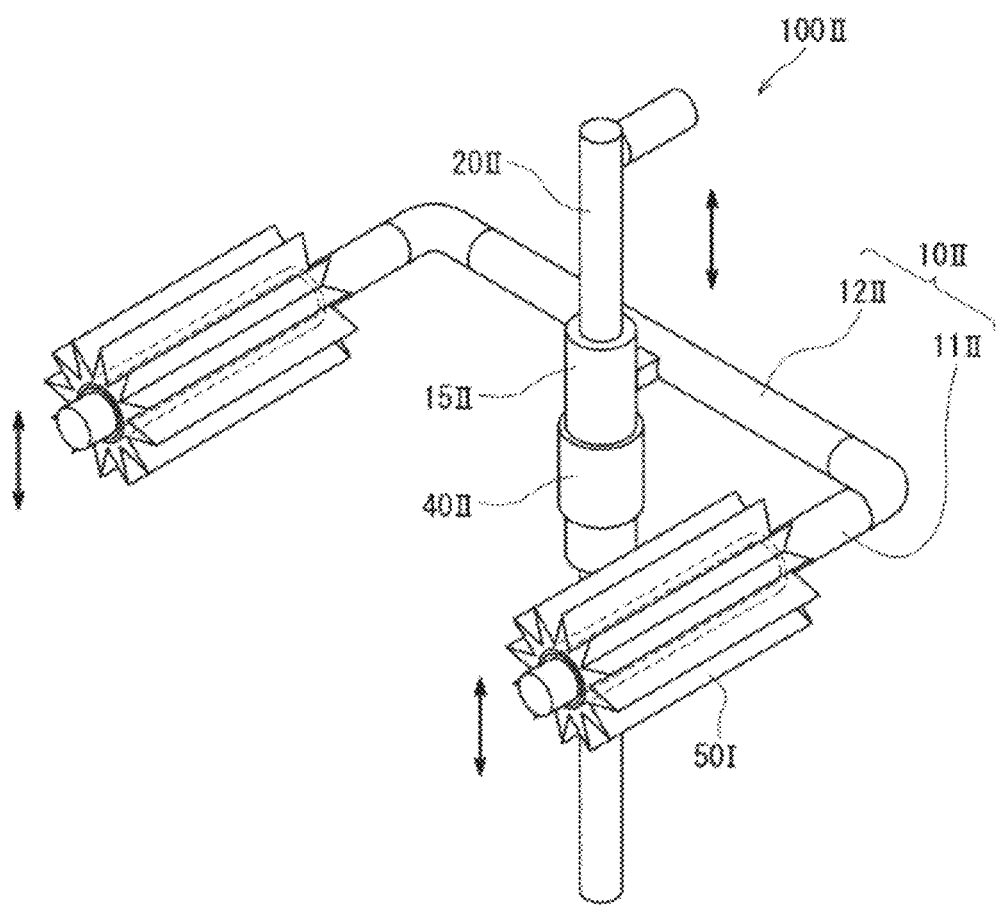
FIG. 16 is a perspective view schematically showing an example in which each arm portion that is a component of the assist device according to one or more aspects of the present disclosure is brought into contact with an elastic portion.

FIG. 13 is a perspective view schematically showing an example in which each arm portion that is a component of the assist device according to one or more aspects of the present disclosure is moved in the up-down direction. FIG. 14 is a perspective view schematically showing another example in which each arm portion that is a component of the assist device according to one or more aspects of the present disclosure is moved in the up-down direction. FIG. 15 is a perspective view schematically showing an example in which each arm portion that is a component of the assist device according to one or more aspects of the present disclosure is connected to the elastic portion. FIG. 16 is a perspective view schematically showing an example in which each arm portion that is a component of the assist device according to one or more aspects of the present disclosure is brought into contact with the elastic portion.

For example, the assist device can be implemented on the premise that the arm portion 10 is movable up and down along the longitudinally extending direction of the supporting pole portion 20. According to this premise, the supporting portion 11 that is a component of the arm portion 10 capable of contacting the armpit 220 can be moved downward along the longitudinally extending direction of the supporting pole portion 20. Consequently, it is possible to smoothly perform heavy muscular work in a state in which the supporting portion 11 and the armpit 220 contact each other (including heavy muscular work with the upper extremity 230 positioned relatively low), and/or work in a forward leaning posture.

Moreover, since the elastic portion 40 capable of contacting or connecting to the arm portion 10 provides an elastic force in the opposite direction to the direction of gravity, the supporting portion 11 as a component of the arm portion 10 which has been moved downward once can be moved upward using the elastic force. Therefore, it is possible to more suitably provide the assist force to the worker 200 using the elastic force of the elastic portion 40 in addition to the reaction force in the opposite direction to the direction of gravity in the supporting portion 11.

Note that, in one aspect in which the arm portion 10 including the supporting portion 11 is moved up and down along the longitudinally extending direction of the supporting pole portion 20, and when the arm portion 10 and the elastic portion 40 are brought into contact with or connected to each other, it is possible to adopt, for example, the following implementations.

In one aspect, an arm portion 10I can have a supporting portion 11I and a shaft part 12I continuous with the supporting portion 11I, and the shaft part 12I be rotatable (see FIG. 13).

In one aspect, the assist device is implemented on the premise that the shaft part 12I as a component of the arm portion 10I is axially rotatable. Specifically, the shaft part 12I can be configured such that the shaft part 12I extends in a different direction, for example, a perpendicular direction to the longitudinally extending direction of the supporting portion 11I, in the same plane, and one end of the supporting portion 11I is continuous with one end of the shaft part 12I.

Moreover, when putting an assist device 100I on the worker, the shaft part 12I can be arranged across the back of the worker to face the back. Further, in one example, the shaft part 12I has a securing portion 13I securely connected to the supporting pole portion 20I, and a movable portion 14I positioned at least one side of the securing portion 13I.

For example, the arm portion 10I including the shaft part 12I can be moved in the up-down direction by the axial rotation of the shaft part 12I. Since the shaft part 12I and the supporting portion 11I are continuously connected, it is possible to move the supporting portion 11I in the up-down direction with the axial rotation of the shaft part 12I.

Moreover, the supporting pole portion 20I can be arranged to intersect the arm portion 10I, one end 41I of an elastic portion 40I can be connected to the supporting portion 11I, and another end 42I can be connected to a predetermined part 21I of the supporting pole portion 20I in a higher position than the supporting portion 11I.

According to the above configuration, the elastic portion 40I can be arranged at a higher position than the supporting portion 11I. Therefore, in order to provide an elastic force in the opposite direction to the direction of gravity, the elastic portion 40I can change into a compressed state after once being stretched. As one example, a rubber member, a tension coil spring or the like can be used as the elastic portion 40I.

Consequently, the supporting portion 11I which has been moved downward once can be moved upward (see FIG. 15).

Alternatively, or additionally, an arm portion 10II can be slidably connected to a supporting pole portion 20II (see FIG. 14).

One end side of the arm portion 10II can be slidably connected to a supporting pole portion 20II. In one example, if the supporting pole portion 20II is long, the arm portion 10II includes a sliding part 15II, and the sliding part 15II can be connected to partly surround the outer periphery of the long supporting pole portion 20II. Moreover, the sliding part 15II of the arm portion 10II can be a partially protruding part from a shaft part 12II. The protruding part can extend in a different direction, for example, a perpendicular direction to the longitudinally extending direction of the shaft part 12II.

The arm portion 10II including the sliding part 15II makes the arm portion 10II as a whole slidable with respect to the supporting pole portion 20II.

Consequently, with sliding of the arm portion 10II, the supporting portion 11II as a component thereof can be moved in the up-down direction. Note that the arm portion 10II can not only slide along the longitudinal direction of the supporting pole portion 20II, but also slide axially rotatably with respect to the short direction of the supporting pole portion 20II.

Further, an elastic portion 40II can be arranged under the arm portion 10II to be able to contact the slidable arm portion 10II.

According to the above configuration, the elastic portion 40II can be arranged at a lower position than the arm portion 10II including the supporting portion 11II. Therefore, in order to provide an elastic force in the opposite direction to the direction of gravity, the elastic portion 40II can change into a stretched state after once being compressed. As one example, a compressed coil spring or the like can be used as the elastic portion 40II. Consequently, the supporting portion 11II which has been moved downward once can be moved upward (see FIG. 16).

A supporting pole portion 20III can be bendable forward and backward, and the bendable supporting pole portion 20III be positioned to be able to face a waist 250 of the worker 200.

Figure 17:
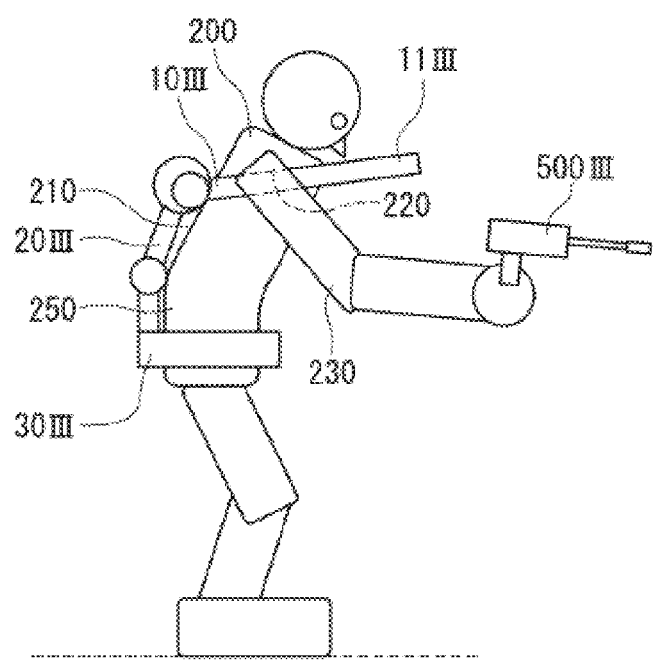
FIG. 17 is a side view schematically showing the assist device according to one or more aspects of the present disclosure having a supporting pole portion bendable forward and backward.

FIG. 17 is a side view schematically showing the assist device according to one or more aspects of the present disclosure, having a supporting pole portion bendable forward and backward.

The supporting pole portion 20III that is a component of an assist device 100III is bendable forward and backward.

According to the above characteristic, in work performed in a forward leaning posture using a tool 500III and/or heavy muscular work performed in a state in which the supporting portion 11III and the armpit 220 contact each other (including heavy muscular work performed with the upper extremity 230 positioned relatively low), in heavy muscular work performed with the upper extremity 230 positioned relatively low, when the back 210 of the worker 200 is curved forward, it is possible to arrange the supporting pole portion 20III along the curved back 210. Consequently, it is possible to improve the work efficiency of the worker 200 during the work.

Note that the present disclosure is not limited to the embodiment described as an example, and various modifications and design changes can be made within a scope that does not depart from the gist of the present disclosure.

Note that one or more aspects of the present disclosure as described above includes the following:

First Example

An assist device capable of generating an assist force for a worker, and including a supporting portion capable of supporting an armpit of the worker.

Second Example

The assist device according to the first example, wherein the supporting portion is arranged to be independent of a motion of an upper extremity of the worker.

Third Example

The assist device according to the first example or the second example, wherein the supporting portion is a reaction force receiving portion against a load force of a grasped object by the worker.

Fourth Example

The assist device according to any one of the first example to the third example, wherein the supporting portion is positioned directly below the armpit.

Fifth Example

The assist device according to any one of the first example to the fourth example, wherein the supporting portion is long, and a longitudinal part of the supporting portion extends in a direction intersecting the direction of gravity.

Sixth Example

The assist device according to any one of the first example to the fifth example, wherein the supporting portion is arranged along a side of a trunk of the worker to protrude to a front of the trunk.

Seventh Example

The assist device according to any one of the first example to the sixth example, wherein the supporting portion is capable of supporting both of two armpits of the worker.

Eighth Example

The assist device according to any one of the first example to the seventh example, further having an arm portion including the supporting portion, and a supporting pole portion connected to the arm portion, wherein the supporting pole portion extends along a back of the worker.

Ninth Example

The assist device according to any one of the first example to the eighth example, wherein the supporting pole portion is a reaction force transmitting portion against a load force of a grasped object by the worker.

Tenth Example

The assist device according to the eighth example or the ninth example, wherein the arm portion is capable of moving up and down along a longitudinally extending direction of the supporting pole portion, and capable of contacting or connecting to an elastic portion that provides an elastic force in the opposite direction to the direction of gravity.

Eleventh Example

The assist device according to the tenth example, wherein the arm portion has the supporting portion, and a shaft part continuous with the supporting portion, and the shaft part is axially rotatable.

Twelfth Example

The assist device according to the tenth example or the eleventh example, wherein the supporting pole portion is arranged to intersect the arm portion, one end of the elastic portion is connected to the supporting portion, and another end is connected to a predetermined part of the supporting pole portion in a higher position than the supporting portion.

Thirteenth Example

The assist device according to any one of the tenth example to the twelfth example, wherein the arm portion is slidably connected to the supporting pole portion.

Fourteenth Example

The assist device according to any one of the tenth example to the thirteenth example, wherein the elastic portion is arranged under the arm portion to be able to contact the arm portion.

Fifteenth Example

The assist device according to any one of the first example to the fourteenth example, further having a shock absorbing member that surrounds an outer main surface of the supporting portion.

Sixteenth Example

The assist device according to the fifteenth example, having an axially rotatable cylindrical portion that surrounds the outer main surface of the supporting portion, wherein the shock absorbing member surrounds the cylindrical portion.

Seventeenth Example

The assist device according to any one of the eighth example to the sixteenth example, wherein the supporting pole portion is bendable forward and backward, and the bendable supporting pole portion is positioned to be able to face a waist of the worker.

Eighteenth Example

The assist device according to any one of the eighth example to the seventeenth example, further having a wearable portion that is connected to the supporting pole portion, and is wearable on the worker.

Nineteenth Example

The assist device according to the eighteenth example, wherein the wearable portion is a reaction force transmitting portion against a load force of a grasped object by the worker.

Twentieth Example

The assist device according to any one of the first example to the nineteenth example, wherein the assist device is used for at least one of heavy muscular work performed in a state in which the supporting portion and the armpit contact each other, and work performed in a forward leaning posture.

Twenty First Example

The assist device according to the twentieth example, wherein the heavy muscular work includes transport work of a heavy object of not less than 5 kg and not more than 25 kg.

Twenty Second Example

The assist device according to any one of the first example to the twenty first example, wherein the assist device is wearable so that the assist device can be worn on the worker.

Twenty Third Example

The assist device according to any one of the first example to the twenty second example, wherein the assist device is used for assembling an automobile.

INDUSTRIAL APPLICABILITY

The assist device according to one or more aspects of the present disclosure can be suitably used in assembling an automobile.

The invention claimed is:

1. An assist device, comprising: a supporting portion configured to support an armpit of a worker, wherein the assist device is configured to generate an assist force for the worker; further comprising a shock absorbing member that surrounds an outer main surface of the supporting portion; further comprising an axially rotatable cylindrical portion that surrounds the outer main surface of the supporting portion, wherein the shock absorbing member surrounds the axially rotatable cylindrical portion.

2. The assist device according to claim 1, further comprising an arm portion including the supporting portion, and a supporting pole portion connected to the arm portion, wherein the supporting pole portion is configured to extend along a back of the worker.

3. The assist device according to claim 2, wherein the arm portion is capable of moving up and down along a longitudinally extending direction of the supporting pole portion, and capable of contacting or connecting to an elastic portion that provides an elastic force in an opposite direction to a direction of gravity.

4. The assist device according to claim 3, wherein the arm portion includes the supporting portion and a shaft part continuous with the supporting portion, and the shaft part is axially rotatable.

5. The assist device according to claim 4, wherein the supporting pole portion is arranged to intersect the arm portion, a first end of the elastic portion is connected to the supporting portion, and a second end is connected to a predetermined part of the supporting pole portion in a higher position than the supporting portion.

6. The assist device according to claim 3, wherein the arm portion is slidably connected to the supporting pole portion.

7. The assist device according to claim 6, wherein the elastic portion is arranged under the arm portion to be able to contact the arm portion.

8. The assist device according to claim 2, further comprising a wearable portion that is connected to the supporting pole portion and is configured to be wearable on the worker.

9. The assist device according to claim 8, wherein the wearable portion is a reaction force transmitting portion against a load force of a grasped object by the worker.

10. The assist device according to claim 2, wherein the supporting pole portion is a reaction force transmitting portion against a load force of a grasped object by the worker.

11. The assist device according to claim 2, wherein the supporting pole portion is bendable forward and backward, and the supporting pole portion is positioned to be able to face a waist of the worker.

12. The assist device according to claim 1, wherein the supporting portion is configured to be independent of a motion of an upper extremity of the worker.

13. The assist device according to claim 1, wherein the supporting portion is a reaction force receiving portion against a load force of a grasped object by the worker.

14. The assist device according to claim 1, wherein the supporting portion is configured to be positioned directly below the armpit.

15. The assist device according to claim 1, wherein a longitudinal part of the supporting portion extends in a direction intersecting a direction of gravity.

16. The assist device according to claim 1, wherein the supporting portion is configured to be arranged along a side of a trunk of the worker to protrude to a front of the trunk.

17. The assist device according to claim 1, wherein the supporting portion is configured to be capable of supporting both of two armpits of the worker.

18. The assist device according to claim 1, wherein the assist device is configured to be wearable so that the assist device can be worn on the worker.

* * * * *